United States Patent [19]
Yorkey

[11] Patent Number: 5,645,060
[45] Date of Patent: Jul. 8, 1997

[54] METHOD AND APPARATUS FOR REMOVING ARTIFACT AND NOISE FROM PULSE OXIMETRY

[75] Inventor: Thomas J. Yorkey, San Ramon, Calif.

[73] Assignee: Nellcor Puritan Bennett Incorporated, Pleasanton, Calif.

[21] Appl. No.: 490,315

[22] Filed: Jun. 14, 1995

[51] Int. Cl.⁶ .................................................. A61B 5/00
[52] U.S. Cl. ..................................... 128/633; 356/41
[58] Field of Search ............................. 128/633, 664, 128/665, 666; 356/41

[56] References Cited

U.S. PATENT DOCUMENTS

| | | | |
|---|---|---|---|
| 4,714,341 | 12/1987 | Hamaguri et al. | 128/633 |
| 4,955,379 | 9/1990 | Hall | 128/633 |
| 5,078,136 | 1/1992 | Stone et al. | 128/633 |
| 5,285,782 | 2/1994 | Prosser | 128/633 |
| 5,351,685 | 10/1994 | Potratz | 128/633 |
| 5,368,026 | 11/1994 | Swedlow et al. | 128/633 |
| 5,385,143 | 1/1995 | Aoyagi | 128/633 |
| 5,482,036 | 1/1996 | Diab et al. | 128/633 |

FOREIGN PATENT DOCUMENTS

94/03102  2/1994  WIPO ................................. 356/41

*Primary Examiner*—Lee S. Cohen
*Assistant Examiner*—Eric F. Winakur
*Attorney, Agent, or Firm*—Townsend and Townsend and Crew LLP

[57] ABSTRACT

Motion compensation is based on analysis of intensity signals received by detectors, without separately measuring a motion signal, without providing feedback to cancel the motion signal and without attempting to mathematically eliminate the motion signal. Instead, the present invention mathematically recognizes the presence of the motion signal and recognizes a few key characteristics of the motion signal and makes corresponding assumptions. First, it is recognized that the motion/noise in each wavelength signal is proportional. Second, it is assumed that the blood pulse signal is not affected by motion.

17 Claims, 3 Drawing Sheets

METHOD AND APPARATUS FOR REMOVING ARTIFACT AND NOISE FROM PULSE OXIMETRY

BACKGROUND

The present invention relates to a pulse oximeter for detecting blood oxygenation, and in particular to the elimination of motion artifact which may affect the detected blood oxygenation signal.

Pulse oximeters typically measure and display various blood flow characteristics including but not limited to blood oxygen saturation of hemoglobin in arterial blood, volume of individual blood pulsations and the rate of blood pulsations corresponding to each heartbeat of the patient. The oximeters pass light through human or animal body tissue where blood perfuses the tissue such as a finger, an ear, the nasal septum or the scalp, and photoelectrically sense the change in absorption of light in the tissue. The amount of light absorbed is then used to calculate the amount of blood constituent being measured.

The light passed through the tissue is selected to be of one or more wavelengths that is absorbed by the blood in an amount representative of the amount of the blood constituent present in the blood. The amount of transmitted light passed through the tissue will vary in accordance with the changing amount of blood constituent in the tissue and the related light absorption.

The optical signal can be degraded by both noise and motion artifact. One source of noise is ambient light which reaches the light detector. Another source of noise would be electromagnetic coupling from other electronic instruments in the area. Motion of the patient can also affect the signal. For instance, when moving, the coupling between the detector and the skin or the emitter and the skin can be affected, such as by the detector moving away from the skin temporarily, for instance. In addition, since blood is a fluid, it may not move at the same speed as the surrounding tissue, thus resulting in a momentary change in volume at the point the oximeter probe is attached.

Such motion can degrade the signal used for making medical decisions, with the clinician being unaware of it. This is especially true if there is remote monitoring of the patient, the motion is too small to be observed, the clinician is watching the instrument or other parts of the patient and not the sensor site, or in a fetus where motion is hidden.

In one oximeter system described in U.S. Pat. No. 5,025,791, an accelerometer is used to detect motion. When motion is detected, readings influenced by motion are either eliminated or indicated as being corrupted. In a typical oximeter, measurements taken at the peaks and valleys of the blood pulse signal are used to calculate the desired characteristic. Motion can cause a false peak, resulting in a measurement having an inaccurate value and one which is recorded at the wrong time. In U.S. Pat. No. 4,802,486, assigned to Nellcor, the disclosure of which is incorporated herein by reference, an EKG signal is monitored and correlated to the oximeter reading to provide synchronization to limit the effect of noise and motion artifact pulses on the oximeter readings. This reduces the chances of the oximeter locking on to a periodic motion signal. Still other systems, such as that set forth in U.S. Pat. No. 5,078,136, assigned to Nellcor, the disclosure of which is incorporated herein by reference, use signal processing in an attempt to limit the effect of noise and motion artifact. The '136 patent, for instance, uses linear interpolation and rate of change techniques to analyze the oximeter signal.

The nature of oximetry readings impose a number of difficulties in dealing with noise. The oximeter relies on mathematical analysis of the readings at two different wavelengths. Because different amounts of light are absorbed at each wavelength, the magnitude of the motion artifact due to the same motion will be different for each signal. This is complicated by the fact that the lights are alternately pulsed, and thus each is influenced by a different amount of motion, since the motion varies with time.

One system, set forth in PCT Publication No. WO 92/15955 (Vital Signals, Inc.) correlates the non-noise portion of two wavelength signals and generates a noise reference signal. The noise reference signal is then provided to an adaptive noise canceler to eliminate the noise from the desired signal.

U.S. Pat. No. 4,714,341 discloses the use of three different wavelengths, rather than two, in order to detect when noise is present. This patent teaches using the first and second wavelength signals to produce a first oxygen saturation value, and then using the first and third wavelength signals to produce a second oxygen saturation value. The two calculated values are then compared. If the values are equal, as they should be absent motion, the signal is presumed to be good. If the values are different, the signal is assumed to contain motion and is disregarded.

SUMMARY OF THE INVENTION

The present invention is based on analysis of the signal intensity received by the detectors, without separately measuring the motion signal, without providing feedback to cancel the motion signal and without attempting to mathematically eliminate the motion signal. Instead, the present invention mathematically recognizes the presence of the motion signal and recognizes a few key characteristics of the motion signal. First, although the magnitude of the effect of motion on the signal intensity for each wavelength will be different, the change in the logarithm of the motion component will be approximately the same (for signals at approximately the same time). This allows the motion component to be cancelled out in a ratiometric equation. Second, it is assumed that the blood pulse signal is not affected by motion. This second assumption is more of an approximation, since the blood pulse signal is somewhat affected by motion, which can actually change the blood volume characteristics at any point in the patient.

The invention recognizes that the intensity signal for each of the wavelengths includes a time-varying motion term, and that this time-varying motion term is proportional for each of the wavelengths. In addition, each wavelength signal occurs close enough in time that the motion should not vary noticeably, and can assumed to be the same for each signal. Given this recognition, it is possible to determine the saturation by including an appropriate time-varying motion term in the equations to determine saturation. This can be done for either a two wavelength or a three wavelength embodiment.

In one two-wavelength embodiment, a time-variable motion term corresponding to motion noise is included in the equations representing the intensity for the first and second wavelength signals. The logarithm of each equation is taken, and then differentiated. The equations are then solved to determine the saturation value by assuming that the motion is a time varying function that is assumed to be independent of the concentration, and not vary in the time between signals.

In an alternate embodiment, radiation of three discrete, different wavelengths is directed through a portion of a patient. The amount of the radiation exiting the patient is detected for each of the three wavelengths, producing three intensity signals. Each intensity signal is represented by an equation which is a function of a saturation, the wavelength corresponding to the intensity signal and corresponding coefficients. In addition, a motion term is added to the equation which is assumed to be variable with time and is assumed to be the same for each of the different wavelength intensity signals. The three equations are then solved to determine the saturation value, preferably using matrix algebra.

For a fuller understanding of the nature and advantages of the invention, reference should be made to the ensuing detailed description taken in conjunction with the accompanying drawings.

DETAILED DESCRIPTION OF THE PREFERRED EMBODIMENTS

Figure 1A:
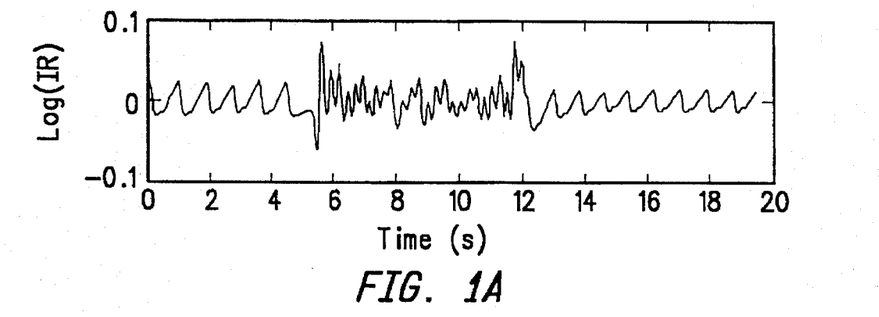
FIGS. 1A–1D are diagrams of an intensity signal showing the effects of pulsatile flow and motion noise.
Figure 1B:
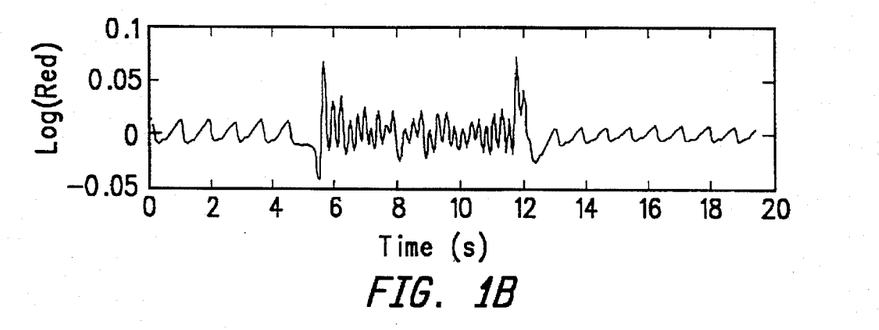
Figure 1C:
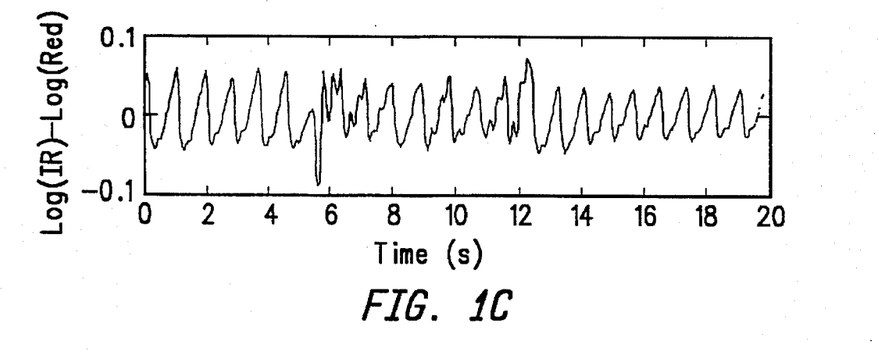
Figure 1D:
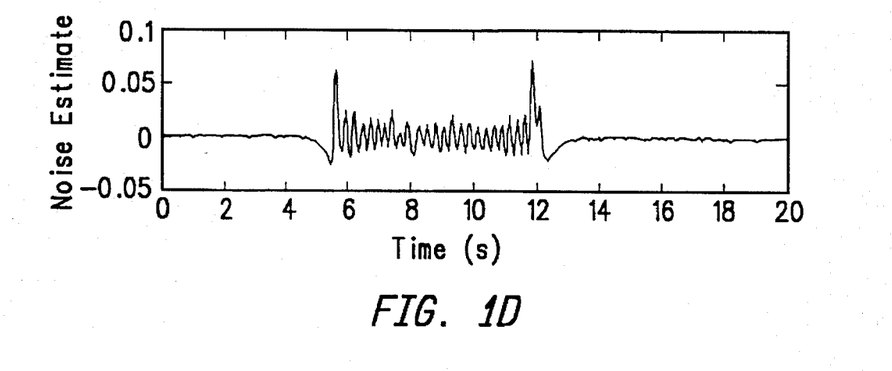

FIGS. 1A–1D illustrate aspects of a pulse oximeter signal which the present invention takes advantage of. FIG. 1A shows the logarithm of a detected infrared signal. FIG. 1B shows the logarithm of a detected red wavelength signal. For both of these figures, the signal includes motion occurring in the interval of 5–12 seconds. Otherwise, both the red and infrared signals are noise-free optical signals. FIG. 1C shows the result of a subtraction between the signals in FIGS. 1A and 1B. As this illustrates, the subtraction cancels out the noise. This is because the data exists in logarithm form, and the motion corruption is additive. Accordingly, in addition to calculating saturation, the difference waveform (FIG. 1C) can be scaled, and then subtracted from either the logarithm of the IR or red signal to obtain an estimate of the motion noise. FIG. 1D shows this estimate.

Figure 2A:
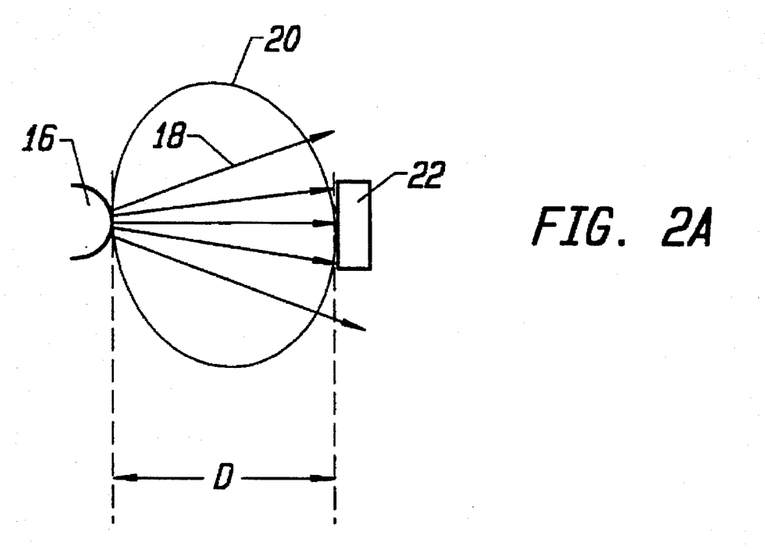
FIGS. 2A and 2B are diagrams illustrating the effect of motion on the path length of emitted light, and thus on the intensity of received light.

FIG. 2A illustrates one possible example of how motion can effect the intensity signal. A light emitter 16 is shown emitting rays 18 through a patient's finger 20. This is detected by a detector 22. As can be seen, the distance from the emitter to the detector, D, will determine the amount of light emitted by the emitter reaching the detector, since there will be a natural spreading effect of non-collimated light rays. The farther away the detector is, the more spreading results.

Figure 2B:
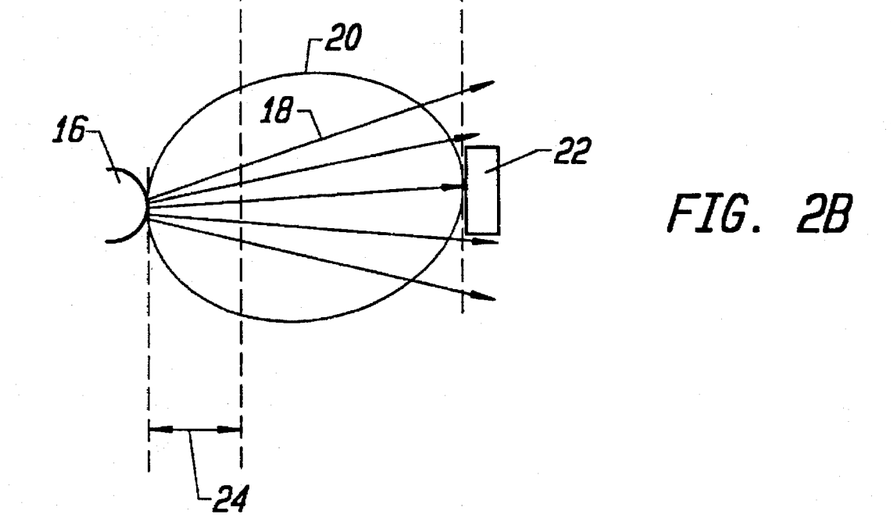

FIG. 2B illustrates another example showing how motion of a finger can compress and widen the finger (exaggerated in the figure) and temporarily cause the light emitter 16 to move away from the detector an additional distance indicated by arrow 24. This additional distance will cause less of the light to reach the detector, since there will be more spreading of the light emitted at this larger distance. This will result in a lower intensity waveform being detected by the detector. Alternately, compression could result in a higher intensity waveform. Motion and noise can take other forms as well, and can vary for other reasons than non-collimated light rays. For instance, the emitter and detector could be slightly misaligned.

The present invention recognizes that the calculation for determining oxygen saturation by pulse oximetry using the "ratio of ratios" can be assumed to have a motion term which is independent of any particular wavelength. An understanding of this first requires an understanding of how the ratio of ratios is calculated.

Using Lambert-Beer's law as a starting point, equation (1) below is used to determine saturation in pulse oximetry:

$$I(\lambda,t)=I_o(\lambda)\exp(-(s\beta_o(\lambda)+(1-s)\beta_x(\lambda))l(t)) \quad (1)$$

where:

$\lambda$=wavelength t=time $I_o$=intensity of light transmitted

I=intensity of light detected s=oxygen saturation $\beta_o$, $\beta_x$=empirically derived absorption coefficients for oxygenated and deoxygenated hemoglobin, respectively l(t)=a combination of concentration and path length from emitter to detector as a function of time The traditional approach is to solve for ratio of ratios and then calculate saturation.

Take natural logarithm of equation (1) for IR and Red:

$$\log I = \log I_o - (s\beta_o + (1-s)\beta_x)l \quad (2)$$

Differentiate equation (2) with respect to time:

$$\frac{d\log I}{dt} = -(s\beta_o + (1-s)\beta_r)\frac{dl}{dt} \quad (3)$$

Divide Red (3) by IR (3)

$$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})} \quad (4)$$

For a discrete time sample, equations of the above form can be rewritten by noting:

$$\frac{d\log I(\lambda,t)}{dt} \cong \log I(t_2,\lambda) - \log I(t_1,\lambda)$$

Using logA–logB=logA/B, the above equation can then be written as:

$$\frac{d\log I(\lambda)}{dt} = \log\left(\frac{I(t_2,\lambda)}{I(t_1,\lambda)}\right)$$

So, $$\frac{\frac{d\log I(\lambda_R)}{dt}}{\frac{d\log I(\lambda_{IR})}{dt}} = \frac{\log\left(\frac{I(t_1,\lambda_R)}{I(t_2,\lambda_R)}\right)}{\log\left(\frac{I(t_1,\lambda_{IR})}{I(t_2,\lambda_{IR})}\right)} \equiv R \quad (5)$$

Where R is the "ratio of ratios."

Solving (4) for s using (5) gives:

$$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}$$

From (5) note R can be calculated using two points corresponding to measurements at two different times, t. Alternately, a family of points can be used. To see this latter point define:

$$x(t) = \log\left(\frac{I(t+\Delta t, \lambda_{IR})}{I(t, \lambda_{IR})}\right)$$

$$y(t) = \log\left(\frac{I(t+\Delta t, \lambda_R)}{I(t, \lambda_R)}\right)$$

Then, equation (5) can be written as:

$$y(t) = Rx(t)$$

and for a family of points over time this will describe a cluster of points that define a best-fit line of y versus x with a slope given by R.

The present invention modifies the above equations by recognizing that a term can be added to account for motion and noise. In particular, the motion and noise component can be represented by a function which varies with time and is wavelength-independent. This recognition allows a mathematical solution to isolate and eliminate the motion and noise components without requiring prior art methods such as separately measuring the motion.

Motion. For example, to account for motion and noise, we can modify equation (1) by multiplying by a time varying function $\eta(t)$ representing wavelength-independent motion or noise. This gives the following equation:

$$I(\lambda,t) = I_o(\lambda)\eta(t)\exp(-(s\beta_o(\lambda)+(1-s)\beta_r(\lambda))l(t)) \quad (6)$$

We can then solve for s using the same steps as used above. First, we take the logarithm:

$$\log I = \log I_o + \log \eta - (s\beta_o + (1-s)\beta_r)l$$

Next, we differentiate with respect to time:

$$\frac{d\log I}{dt} = \frac{d\log \eta}{dt} - (s\beta_o + (1-s)\beta_r)\frac{dl}{dt} \quad (7)$$

Then, we determine the ratio of Red to IR:

$$\frac{d\log I(\lambda_r)/dt}{d\log I(\lambda_{IR})/dt} = \frac{d\log\eta/dt - (s\beta_o(\lambda_R) + (1-s)\beta_r(\lambda_R))\frac{dl}{dt}}{d\log\eta/dt - (s\beta_o(\lambda_{IR}) + (1-s)\beta_r(\lambda_{IR}))\frac{dl}{dt}}$$

Now if $d\log \eta/dt$ is large compare to the other terms the ratio of ratios will be driven towards unity, driving s towards a wavelength-dependant constant. So because in this model optical coupling due to motion appears identically in both wavelengths, its presence drives the saturation to this wavelength-dependant constant.

The present invention thus allows a calculation of blood oxygen saturation by mathematically recognizing the motion signal. This enables a solution which does not require separately measuring the motion signal, providing feedback to cancel the motion signal, or attempting to mathematically eliminate the motion signal. Set forth below are two preferred embodiments for implementing the present invention, one using three wavelengths of light and another using two wavelengths.

A Three-wavelength Solution

Let $\lambda_o$ be some other wavelength (not IR or Red). Now take the logarithm and differentiate this third wavelength, obtaining (7). One approach might be to difference IR with this new wavelength, and similarly with Red. The problem with differencing is that R could become infinite when:

$$\frac{d}{dt}\log I(\lambda_{IR}) - \frac{d}{dt}\log I(\lambda_o) = 0.$$

Here is a better solution. Rewrite (7) as:

$$\frac{d\log I}{dt} = \frac{d\log\eta}{dt} + (\beta_r - \beta_o)s\frac{dl}{dt} - \beta_r\frac{dl}{dt}$$

Now to introduce some matrix algebra, define:

$$b_i = \frac{d}{dt}\log I(\lambda_i)$$

$$u = \frac{dl}{dt}$$

$$m = \frac{d}{dt}\log\eta$$

$$c_{1j} = \beta_r(\lambda_j) - \beta_o(\lambda_j)$$

$$c_{2j} = \beta_r(\lambda_j)$$

With this notation $$\begin{bmatrix} b_1 \\ b_2 \\ b_3 \end{bmatrix} = \begin{bmatrix} c_{11} & c_{21} & 1 \\ c_{12} & c_{22} & 1 \\ c_{13} & c_{23} & 1 \end{bmatrix} \begin{bmatrix} su \\ u \\ m \end{bmatrix}$$

$$b = Cx$$

$$x = C^{-1}b$$

$$s = x_1/x_2$$

$$m = x_3$$

So as long as C is full rank, there is no difficulty in solving for saturation and the optical coupling terms uniquely. In other words, you can now solve for m exactly because there is no wavelength where $b_1 = b_2 = b_3$ for a given saturation.

Note a calibration set of extinction coefficients are needed for this third wavelength, but also note that the best new wavelength is one that gives the highest condition number to C, which is not necessarily the isobestic point. The calibration coefficients for the third wavelength are constrained by the coefficients for the first two wavelengths. When there is no motion, the saturation calculated using two wavelengths and three wavelengths should be the same.

This optical coupling method will be less accurate when the lumped concentration path-length term becomes wavelength dependent, then the dependence no longer ratios away in calculating saturation. Also, there is no reason to believe that u will look anything like a typical pulse oximetry waveform during motion since path-length and concentration will be varying with the motion, and these effects will be seen in u, but s will still be the correct saturation.

A Two-wavelength Solution

With two wavelengths we have:

$$\begin{bmatrix} b_1 \\ b_2 \end{bmatrix} = \begin{bmatrix} c_{11} & c_{21} & 1 \\ c_{12} & c_{22} & 1 \end{bmatrix} \begin{bmatrix} su \\ u \\ m \end{bmatrix} \quad (8)$$

Two equations and three unknowns. One approach is to return to calculating R by rewriting (8):

$$b_1 = v + m$$

$$b_2 = Rv + m$$

where m is the motion term, as defined earlier, R is the ratio of ratios, and v is the signal with no motion.

There are two key assumptions which make the solution possible. First, although the magnitude of the effect of motion on each intensity signal will be different, the change in the logarithm of the motion component at two different times will be the same (which assumes the different time signal samples are adjacent or close together in time). This allows the motion component to be cancelled out in a ratiometric equation. The second assumption is that the motion does not cause any effect on the remainder of the equation. There is some effect, since motion can change the pulse flow characteristics of the blood, but this is typically a small effect compared to the motion when there is significant motion present. By assuming that the motion has no effect on any elements of the concentration measurement, we assume that v and m are not related.

Another assumption is that the amount of motion is the same at the time of both intensity signal measurements for the two wavelengths. This is a reasonable assumption since the typical motion signal varies at a rate of around 1 Hz, while the light pulsing frequency is typically at a rate of 1200 Hz.

Assuming v and m are independent over time, (v,m)=0 for some defined inner product. Substituting for v and m yields:

$$\left( \frac{b_2 - b_1}{R - 1}, \frac{b_2 - Rb_1}{R - 1} \right) = 0$$

Solving for the R that solves this equality yields:

$$R = \frac{\langle b_2 - b_1, b_1 \rangle}{\langle b_2 - b_1, b_2 \rangle}$$

There are two problems with this approach.

When R approaches one, $b_2-b_1$ approaches zero, and the above equation approaches zero divided by zero. This fact is not in itself a total problem for when $b_2-b_1$ does approach zero you simply use R=1.

A more limiting problem is the assumption that (v,m)=0. Certainly the motion signal is independent of the arterial pulsatile signal, but during motion, v also has path-length concentration effects in it that are highly correlated with m, thus biasing R away from its true value.

Figure 3:
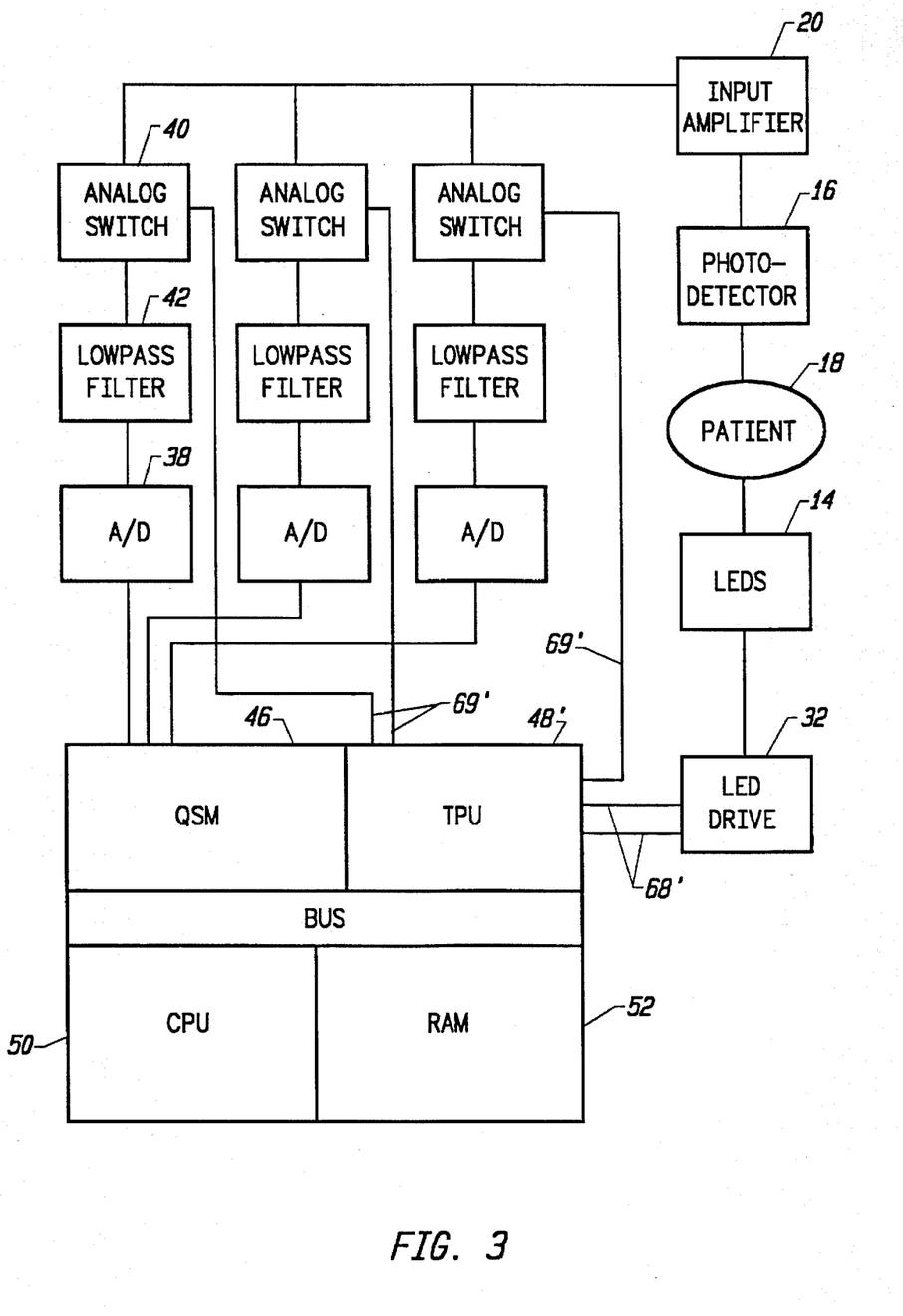
FIG. 3 is a block diagram of a system according to the present invention.

FIG. 3 is a block diagram of one embodiment of a pulse oximeter implementing the present invention. Light from LEDs 14 passes into patient tissue 18, and after being transmitted through or reflected from tissue 18, the light is received by photosensor 16. Either two or three LEDs can be used depending upon the embodiment of the present invention. Photosensor 16 converts the received energy into an electrical signal, which is then fed to input amplifier 20.

Light sources other than LEDs can be used. For example, lasers could used, or a white light source could be used with appropriate filters either at the transmitting or receiving ends.

Time Processing Unit (TPU) 48 sends control signals 68 to the LED drive 32, to alternately activate the LEDs. Again, depending on the embodiment, the drive may control two or three LEDs.

The signal received from input amplifier 20 is passed through three different channels as shown in the embodiment of FIG. 3, for three different wavelengths. Alternately, two channels for two wavelengths could be used. Each channel includes an analog switch 40, a low pass filter 42, and an analog to digital (A/D) converter 38. Control lines 69 from TPU 48 select the appropriate channel at the time the corresponding LED 14 is being driven, in synchronization. A queued serial module (QSM) 46 receives the digital data from each of the channels. CPU 50 transfers the data from QSM 46 into RAM 52 as QSM 46 periodically fills up. In one embodiment, QSM 46, TPU 48, CPU 50 and RAM 52 are part of one integrated circuit, such as a DMC68HC16 microcontroller from Motorola.

The method of the present invention is practiced by CPU 50 on the data in RAM 52 as received through the various channels from photodetector 16. The signal from photodetector 16 is the signal which originated from LEDs 14, as reflected or transmitted by patient 18, and including undesired noise artifact.

As will be understood by those of skill in the art, the present invention can be embodied in other specific forms without departing from the spirit or essential characteristics thereof. For example, saturation could be determined using different mathematical calculations, once it is recognized that the motion term is a function of time that is independent of wavelength and is approximately the same for two adjacent in time signal samples at two different wavelengths. In one example, the mathematical determination could be done by dividing the two intensity equations to eliminate the motion term. Although this would only eliminate the motion from one wavelength equation, this could be done for alternate wavelengths in alternate samples. In a three wavelength embodiment, division of two separate pairs could be done to eliminate the motion signal. Accordingly, the disclosure of the preferred embodiment of the invention is intended to be illustrative, but not limiting, of the scope of the invention which is set forth in the following claims.

What is claimed is:

1. A method for measuring saturation of a blood constituent in a patient comprising the steps of:
    irradiating said patient with electromagnetic radiation of two discrete, different wavelengths;
    sensing an intensity of said radiation for each of said wavelengths after it passes through a portion of said patient to produce first and second intensity signals including motion components; and
    determining said saturation by mathematically manipulating said first and second intensity signals without subtracting said motion components and with the assumptions that
    i) an amount of motion is the same at the same time for each of said intensity signals, and
    ii) the motion components of said intensity signals are proportional to one another.

2. A method for measuring saturation of a blood constituent in a patient comprising the steps of:
    irradiating said patient with electromagnetic radiation of at least two discrete, different wavelengths;
    sensing an intensity of said radiation for each of said wavelengths after it passes through a portion of said patient to produce first and second intensity signals including motion components; and
    determining said saturation by mathematically manipulating said first and second intensity signals with the assumptions that
    i) an amount of motion is the same at the same time for each of said intensity signals, and
    ii) the motion components of said intensity signals are proportional to one another,
    wherein said determining step further includes the assumption that the derivative of the logarithms of the motion components of said intensity signals are the same.

3. A method for measuring saturation of a blood constituent in a patient comprising the steps of:

irradiating said patient with electromagnetic radiation of at least two discrete, different wavelengths;

sensing an intensity of said radiation for each of said wavelengths after it passes through a portion of said patient to produce first and second intensity signal including motion components; and determining said saturation by mathematically manipulating said first and second intensity signals with the assumptions that
 i) an amount of motion is the same at the same time for each of said intensity signals, and
 ii) the motion components of said intensity signals are proportional to one another, wherein the step of determining said saturation further comprises
 representing each of said intensity signals as a function of said saturation, the wavelength corresponding to the intensity signal, and a time-variable motion term corresponding to motion noise, said motion terms being proportional to one another for each of said intensity signals;
 taking the logarithm of each representation of said first and second intensity signals;
 differentiating each logarithm;
 equating the first differentiated logarithm of the first intensity signal to v+m, where m is the portion of the signal due to motion and v is the portion of the signal not due to motion;
 equating the second differentiated logarithm of the second intensity signal to Rv+m, where R is a ratio of first and second wavelength ratios, each wavelength ratio being the logarithm of the ratio of the intensity signal for the wavelength at first and second times;
 expressing said representations as a matrix;
 solving said matrix for R by assuming v and m are independent for some defined inner product; and
 determining said saturation from R.

4. The method of claim 3 further comprising the step of displaying said saturation on a monitor.

5. The method of claim 4 further comprising the step of activating an alarm if said saturation is less than a predetermined amount for a predetermined period of time.

6. A method for measuring saturation of a blood constituent in a patient comprising the steps of:
 irradiating said patient with electromagnetic radiation of at least three discrete, different wavelength;
 sensing the intensity of said radiation for each of said wavelengths after it passes through a portion of said patient to produce first, second and third intensity signals;
 representing each of said intensity signals as a function of said saturation, the wavelength corresponding to the intensity signal, and a time-variable motion term corresponding to motion noise, said motion terms being proportional to one another for each of said intensity signals; and
 solving the three functions to obtain a value for said saturation,
 wherein each of said functions includes a plurality of coefficients, and further comprising the step of determining a set of coefficients for said third intensity signal from a measurement in the absence of motion noise and a determination of said saturation from said first and second intensity signals.

7. A method for measuring saturation of a blood constituent in a patient comprising the steps of:

irradiating said patient with electromagnetic radiation of at least three discrete, different wavelengths;
 sensing the intensity of said radiation for each of said wavelengths after it passes through a portion of said patient to produce first, second and third intensity signals;
 representing each of said intensity signals as a function of said saturation, the wavelength corresponding to the intensity signal, and a time-variable motion term corresponding to motion noise, said motion terms being proportional to one another for each of said intensity signals;
 solving the three functions to obtain a value for said saturation;
 taking the logarithm of each representation of said first, second and third intensity signals;
 differentiating each logarithm;
 putting the differentiated logarithms into a matrix; and
 solving said matrix to obtain said value of said saturation.

8. A method for measuring the saturation of a blood constituent in a patient comprising the steps of:
 irradiating said patient with electromagnetic radiation of three discrete, different wavelengths;
 sensing the intensity of said radiation for each of said wavelengths after it passes through a portion of said patient to produce first, second and third intensity signals;
 representing each of said intensity signals as a function of said saturation, the wavelength corresponding to the intensity signal, and a time-variable motion term corresponding to motion noise, said motion term being the same for each of said intensity signals; and
 solving the three functions to obtain a value for said saturation without subtracting said motion term.

9. A method for measuring the saturation of a blood constituent in a patient comprising the steps of:
 irradiating said patient with electromagnetic radiation of three discrete, different wavelengths;
 sensing the intensity of said radiation for each of said wavelengths after it passes through a portion of said patient to produce first, second and third intensity signals;
 representing each of said intensity signals as a function of said saturation, the wavelength corresponding to the intensity signal, and a time-variable motion term corresponding to motion noise, said motion term being the same for each of said intensity signals; and
 solving the three functions to obtain a value for said saturation;
 wherein each of said functions includes a plurality of coefficients, and further comprising the step of determining a set of coefficients for said third intensity signal from a measurement in the absence of motion noise and a determination of said saturation from said first and second intensity signals.

10. A method for measuring the saturation of a blood constituent in a patient comprising the steps of:
 irradiating said patient with electromagnetic radiation of three discrete, different wavelengths;
 sensing the intensity of said radiation for each of said wavelengths after it passes through a portion of said patient to produce first, second and third intensity signals;
 representing each of said intensity signals as a function of said saturation, the wavelength corresponding to the intensity signal, and a time-variable motion term corresponding to motion noise, said motion term being the same for each of said intensity signals; and solving the three functions to obtain a value for said saturation;

taking the logarithm of each representation of said first, second and third intensity signals; differentiating each logarithm;

putting the differentiated logarithms into a matrix; and solving said matrix to obtain said value of said saturation.

11. A method for measuring the saturation of a blood constituent in a patient comprising the steps of:

irradiating said patient with electromagnetic radiation of two discrete, different wavelengths;

sensing the intensity of said radiation for each of said wavelengths after it passes through a portion of said patient separately to produce first and second intensity signals;

representing each of said intensity signals as a function of said saturation, the wavelength corresponding to the intensity signal, and a time-variable motion term corresponding to motion noise, said motion term being the same for each of said intensity signals;

taking the logarithm of each representation of said first and second intensity signals;

differentiating each logarithm;

equating the first differentiated logarithm of the first intensity signal to v+m, where m is the portion of the signal due to motion and v is the portion of the signal not due to motion;

equating the second differentiated logarithm of the second intensity signal to Rv+m, where R is a ratio of first and second wavelength ratios, each wavelength ratio being the logarithm of the ratio of the intensity signal for the wavelength at first and second times;

expressing said representations as a matrix;

solving said matrix for R by assuming v and m are independent for some defined inner product; and determining said saturation from R.

12. An apparatus for measuring the saturation of a blood constituent in a patient comprising:

first and second emitters, said emitters emitting radiation of first and second different wavelengths;

a detector for sensing an intensity of said light, said detector being mounted relative to said first and second emitters so that said light is detected after it passes through a portion of said patient;

a controller for alternately activating said emitters so that said detector detects the different wavelengths at different times to produce first and second intensity signals including motion components; and control means for determining said saturation by mathematically manipulating said first and second intensity signals without subtracting said motion components and with the assumptions that i) an amount of motion is the same at the same time for each of said intensity signals, and ii) the motion components of said intensity signals are proportional to one another.

13. The apparatus of claim 12 further comprising a display, coupled to said control means, for displaying said saturation.

14. The apparatus of claim 13 further comprising an alarm coupled to said control means for indicating when said saturation is less than a predetermined amount for a predetermined period of time.

15. The apparatus of claim 12 further comprising:

a third emitter for irradiating said patient with electromagnetic radiation of a third discrete, different wavelength;

said controller alternately activating said first, second and third emitters so that said detector produces first, second and third intensity signals;

said control means including means for representing each of said intensity signals as a function of said saturation, the wavelength corresponding to the intensity signal, and a time-variable motion term corresponding to motion noise, said motion term being the same for each of said intensity signals; and means for solving the three functions to obtain a value for said saturation.

16. An apparatus for measuring the saturation of a blood constituent in a patient comprising:

first and second emitters, said emitters emitting radiation of first and second different wavelengths;

a detector for sensing an intensity of said lights. said detector being mounted relative to said first and second emitters so that said light is detected after it passes through a portion of said patient;

a controller for alternately activating said emitters so that said detector detects the different wavelengths at different times to produce first and second intensity signals including motion components; and control means for determining said saturation by mathematically manipulating said first and second intensity signals with the assumptions that i) an amount of motion is the same at the same time for each of said intensity signals, and ii) the motion components of said intensity signals are proportional to one another, wherein said control means operates on the assumption that the derivative of the logarithm of the motion components are the same.

17. A pulse oximeter for measuring the saturation of a blood constituent in a patient comprising:

first and second emitters, said emitters emitting radiation of first and second different wavelengths;

a detector for sensing an intensity of said light, said detector being mounted relative to said first and second emitters so that said light is detected after it passes through a portion of said patient;

a controller for alternately activating said emitters so that said detector detects the different wavelengths at different times to produce first and second intensity signals including motion components; and control means for determining said saturation by mathematically manipulating said first and second intensity signals with the assumptions that i) an amount of motion is the same at the same time for each of said intensity signals, and ii) the motion components of said intensity signals are proportional to one another, wherein said control means further comprises means for representing each of said intensity signals as a function of said saturation, the wavelength corresponding to the intensity signal, and a time-variable motion term corresponding to motion noise, said motion term being the same for each of said intensity signals;

means for taking the logarithm of each representation of said first and second intensity signals;

means for differentiating each logarithm;

means for equating the first differentiated logarithm of the first intensity signal to $v+m$, where m is the portion of the signal due to motion and v is the portion of the signal not due to motion;

means for equating the second differentiated logarithm of the second intensity signal to $Rv+m$, where R is a ratio of first and second wavelength ratios, each wavelength ratio being the logarithm of the ratio of the intensity signal for the wavelength at first and second times;

means for expressing said representations as a matrix;

means for solving said matrix for R by assuming v and m are independent for some defined inner product; and means for determining said saturation from R.

* * * * *